United States Patent [19]

Siebold

[11] Patent Number: Plant 7,568

[45] Date of Patent: Jun. 25, 1991

[54] BEGONIA PLANT NAMED SWEET DIANNE

[75] Inventor: Howard Siebold, Fort Bragg, Calif.

[73] Assignee: Golden State Bulb Growers, Watsonville, Calif.

[21] Appl. No.: 500,256

[22] Filed: Mar. 28, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Begonia plant named Sweet Dianne characterized by its light pink flower color; floriferous habit producing numerous pendulous flowering shoots; distinct sweet fragrance, and its fully double male flowers which have no pollen or male reproductive parts under normal conditions.

2 Drawing Sheets

The present invention relates to a new and distinctive cultivar of Begonia plant known by the cultivar name Sweet Dianne.

The new cultivar was discovered by the inventor Howard Siebold as a seedling from a controlled crossing of an unnamed *Tuberhybrida pendula* as a pollen parent with the cultivar Yellow Sweety as the seed parent.

Asexual reproduction by the inventor by leaf cuttings has reproduced the unique features of the new cultivar through successive propagations.

The following characteristics distinguish the new Begonia from both its parents and other begonias commercially known and used in the floriculture industry.

1. The flowers have a definite and distinct fragrance that is gently sweet but not overpowering. It is often compared to the scent of a fragrant rose bloom. The fragrance is most pronounced at temperatures between 70° and 80° F.

2. The male flowers are fully double and do not produce pollen or visible male reproductive parts under normal growing conditions.

3. The flower color is pink, with the very center of the male blooms being white.

4. The plant habit is full and pendulous with numerous flowering shoots (6–7 or more). Each flowering shoot will produce 4–5 peduncles with 1 to 2 male flowers and 2–3 female flowers on each during the growing season, thereby making Sweet Dianne a very floriferous cultivar.

It is difficult to compare Sweet Dianne with any known Begonia cultivar. Its fragrance is distinctive, and there is no vegetatively reproduced cultivar which possesses its distinct pink color. Although there are pink seed varieties, the pink color is not consistent from generation to generation.

The accompanying colored photographs taken Aug. 24, 1989 illustrate the new cultivar.

The photograph at the top of sheet 1 is a front perspective view showing a typical plant of Sweet Dianne grown in a 10" pot.

The photograph at the bottom of sheet 1 is an enlarged showing of a typical flower.

The photograph on sheet 2 illustrates the upper and under side of typical leaves. The photographs depict the colors as true as it is reasonably possible to obtain in colored reproductions of this type.

The following is a detailed description of my new Begonia cultivar based on plants produced under commercial practices in Capitola, Calif. Color references are made to The Royal Horticultural Society Colour Chart except where general terms of ordinary dictionary significance are used.

Parentage: The begonia cultivar Yellow Sweety (seed parent) × unnamed *Tuberhybrida pendula* (pollen parent).

Propagation:

(A) *Type cutting.*—Leaf cuttings.

(B) *Time to root.*—24–30 days at 21° C. summer; 32–38 days at 21° C. winter.

(C) *Rooting habit.*—Abundant, fibrous, dendritic.

(D) *Time for shoot development.*—Slow; 10–14 weeks in summer and up to 16 weeks in winter. Shoot count is medium to high in summer and less in winter.

Plant description:

(A) *Form.*—Low, mounding, pendulous form; herbaceous.

(B) *Habit of growth.*—Slow, uniform growth with numerous shoots and good branching habit. At full growth the plant is well rounded with a 15–20" height and up to 24" pendulous shoots. The width is approximately 24".

(C) *Foliage.*—Simple, alternate, and borne on semi-rigid 6–8" petioles. (1) Size: At maturity the leaves reach 10–11" from base to apex, and at their widest point the leaves are up to 6½" in width. (2) Shape: Triangular-cordate with acuminate tip between rounded basal lobes. (3) Texture: Firm, crisp, but not brittle; sparsely hirtellous on both surfaces. (4) Margin: Double-serrate margins. (5) Color: Young foliage: Top side 143A; under side 146D. Mature foliage: Top side 146B; under side 147D. (6) Veination: Reticulate.

Flowering description:

(A) *Flowering habits.*—Flowering is presented on a pendulous raceme. Often, but not always, secondary male and female flowers will develop below the primary male and female flowers. Some peduncles will have a single male flower accompanied by a solitary female flower, while others will have matching female flowers per male.

(B) *Natural flowering season.*—The natural flowering season is the summer and fall months.

(C) *Flower buds.*—Flat, nearly round, tending towards bell shaped.

(D) *Flowers borne.*—On small pedicels originating from long (7–9") axillary peduncles, resulting in a solitary male and one or two female flowers, and occasionally secondary male and female flowers as raceme developes.

(E) *Quantity.*—Flowering ranges from 2–5 flowers per peduncle and numerous (3–5) peduncles per shoot, with 5–7 shoots per plant.

(F) Tepals.—(1) Shape: Oval to tear drop shaped. (2) Color: Top side in spring when opening, salmon-pink 48D, fading to 38D and 36D; a white center is revealed when inner tepals are separated; under side, soft pink 48C. (3) Number of tepals: 54–62 on male flowers, 5 on female flowers. (4) Size of tepals: Outer, $2\frac{3}{4}'' \times 2\frac{3}{4}''$; inner $\frac{3}{8}'' \times \frac{3}{8}''$. (5) Flower size: Male, $5'' \times 5''$; female, $3\frac{3}{4}'' \times 3\frac{3}{4}''$.

(G) *Reproductive organs.*—(1) Stamens: None; only modified petals with immature fused male reproductive parts. (2) Pistils: (a) Stigma shape: multilobed, occasionally modified to petals form; color 15A. (b) Style color: 24A. (c) Ovaries: Three in number; $\frac{3}{8}''$–$\frac{5}{8}''$ in diameter; syncarpous, pale green with sheen.

*Disease resistance: Sweet Dianne has shown excellent disease resistance to date.*

I claim:

1. A new and distinct Begonia plant named Sweet Dianne, as illustrated and described.

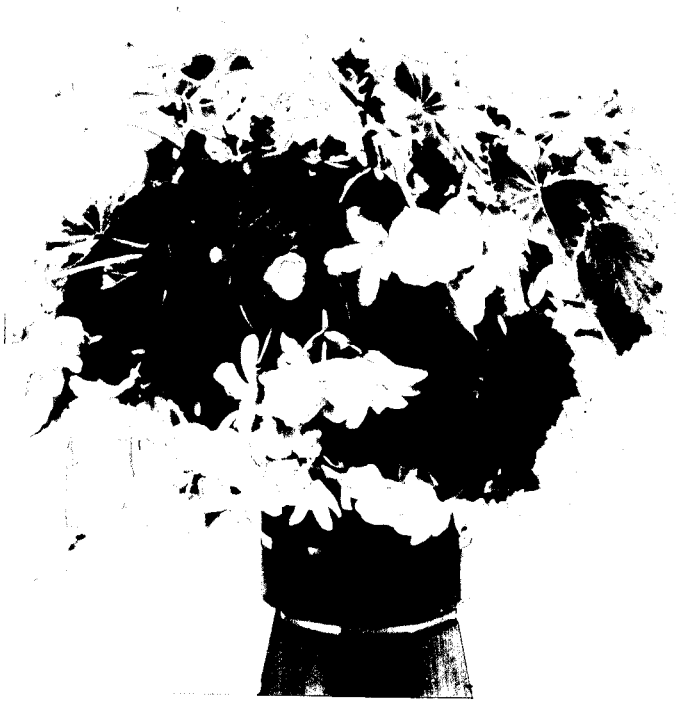

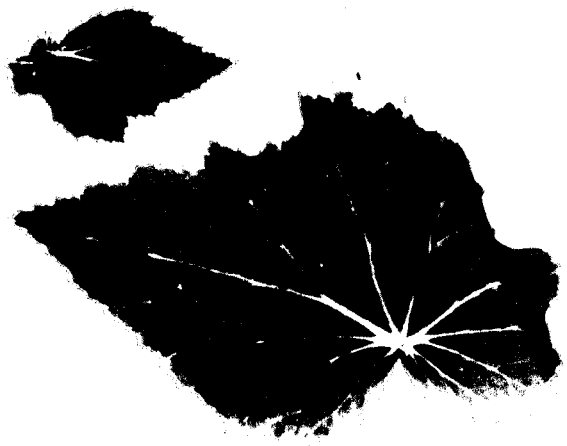

* * * * *